United States Patent [19]

Sklar

[11] 4,071,620

[45] Jan. 31, 1978

[54] STABILIZATION OF OXYGEN SENSITIVE DOSE FORMS

[75] Inventor: Stanley Sklar, Broomall, Pa.

[73] Assignee: American Home Products Corporation, New York, N.Y.

[21] Appl. No.: 758,236

[22] Filed: Jan. 10, 1977

[51] Int. Cl.² .................. A61K 31/00; A61K 31/54
[52] U.S. Cl. .................................. 424/175; 424/247
[58] Field of Search ............................. 424/175, 247

[56] References Cited

PUBLICATIONS

Physicians' Desk Reference — 24th, 1497–1499 (1969).
Physicians' Desk Reference — 19th, 719–720 (1964).

*Primary Examiner*—Stanley J. Friedman
*Attorney, Agent, or Firm*—Joseph Martin Weigman

[57] ABSTRACT

The disclosure is directed to improvement of the stability of oxygen sensitive compounds. Phenothiazines may be stabilized by the use of small amounts of monothioglycerol in the marketable composition. Especially good results are obtained in the stabilization of promethazine formulations with monothioglycerol.

10 Claims, No Drawings

STABILIZATION OF OXYGEN SENSITIVE DOSE FORMS

The invention is directed to antioxidants for use in pharmaceutical compositions of matter in which the active ingredient is oxygen sensitive. It has been found that monothioglycerol (MTG) improves the shelf life of phenothiazines and is particularly effective in promethazine formulations.

The invention comprises in its broadest aspect the substitution of monothioglycerol (MTG) as an antioxidant for sodium metabisulfite and sodium formaldehyde sulfoxylate (SFSO) which have been used for the same purpose. The substitution when made in a promethazine-containing composition of matter resulted in lengthened storage time or shelf life.

One advantage of the invention is that, while it is known that metabisulfite-SFSO degrade in the absence of oxygen, MTG does not. Another advantage of the invention is that MTG is a non-sulfur dioxide ($SO_2$) containing antioxidant. The first disadvantage of $SO_2$ containing antioxidants is that they oxidize to sulfate and promethazine sulfate has limited solubility. The second problem arises as a result of the anaerobic degradation of these compounds to thiosulfate, which also combines with promethazine to yield a highly insoluble salt.

The most closely related prior art is the use of monothioglycerol in Leritine, Sandril and streptomycin sulfate (none of which are phenothiazine) each of which contained monothioglycerol in the amount of 2 milligrams per cubic centimeter (mg/cc), 10 mg/cc and 2.5 mg/cc, respectively.

It is an object of the present invention to provide a method of stabilizing oxygen sensitive compounds.

It is another object of the present invention to provide pharmaceutical compositions of matter containing phenothiazines having improved shelf life.

It is yet another object of the present invention to provide pharmaceutical compositions of matter containing promethazines which have improved shelf life.

This invention relates to the use of monothioglycerol (MTG) as the antioxidant of choice for phenothiazine-containing composition of matter and particularly promethazine hydrochloride injection composition of matter.

Promethazine hydrochloride injection composition of matter has been marketed using a combination antioxidant system of 0.25 mg/cc of sodium metabisulfite and 0.75 mg/cc of SFSO. Under the scope of this invention the antioxidant is changed to MTG which affords the product a great increase in protection against oxidative degradation. Below are listed an existing promethazine production formula of the prior art and a formula modified under the scope of this invention.

|  | PRIOR ART | PRESENT FORMULA |
|---|---|---|
| Promethazine hydrochloride | 25 mg. or 50 mg. | 25 mg. or 50 mg. |
| Sodium Metabisulfite | 0.25 mg. | — |
| SFSO | 0.75 mg. | — |
| EDTA, disodium | 0.099 mg. | 0.099 |
| Calcium Chloride | 0.039 mg. | 0.039 |
| Sodium Acetate | 6.15 mg. | 6.15 |
| Phenol | 5.0 mg. | 5.0 |
| Acetic Acid | adj. to pH 5.0 | adj. to pH 5.0 |
| Monothioglycerol | — | 5.0 mg. - 6.0 mg. |
| Water for Injection | qs. 1.0 cc. | qs. 1.0 cc. |

Promethazine hydrochloride is a member of a chemical class of drugs called phenothiazines of which there are many members. A large number of the drugs are marketed as injectable products. In all these products, in no case is MTG used as the antioxidant. Most commonly used antioxidants are sodium bisulfite, sodium sulfite, SFSO and ascorbic acid, individually or in combination. All these drugs are oxygen sensitive to varying degrees, though some are formulated without an antioxidant. One product stands out in that the ampul formulation contains an antioxidant while the vial does not. The oddity here is that the vial, due to ingress of air, or air injection during use would be expected to require the antioxidant. It is hypothesized that when the company marketing the product evaluated the antioxidant-containing product ($SO_2$-type antioxidant) in vials, the ingressed air resulted in degradation of the antioxidant. The reaction between the active and the degradation by-product, probably sulfate ion, resulted and the product was no longer acceptable, probably due to insoluble formation.

A series of promethazine formulations containing different antioxidants were tested for their oxidation potentials. One formulation stood out as containing the best antioxidant for a promethazine formulation; it was monothioglycerol (MTG).

As a result of the oxidation potential studies, phenergan bulks were prepared using 2 and 5 mg/cc of monothioglycerol as the antioxidant. Preliminary accelerated data of this limited storage indicated that the promethazine and the MTG were generally compatible though a potential rubber compatibility problem was indicated. As a result of this preliminary storage a second larger storage was initiated. The second storage evaluated the six formulations listed below:

1. Promethazine hydrochloride, 50 mg/cc, production formula - control
2. Promethazine hydrochloride, 25 mg/cc, production formula - control
3. Promethazine hydrochloride, 50 mg/cc, with 2 mg/cc MTG
4. Promethazine hydrochloride, 50 mg/cc, with 5 mg/cc MTG
5. Promethazine hydrochloride, 25 mg/cc, with 2 mg/cc MTG
6. Promethazine hydrochloride, 25 mg/cc, with 5 mg/cc MTG Below are Table I showing the physical stability after 17 months and Table II showing physical stability after 29 months of the production promethazine hydrochloride compared with the proposed formulation under the scope of this invention. In Table I, the lower concentration 2 mg/cc MTG, when used in syringes seems inadequate compared to the protection offered at the higher concentration, 5 mg/cc. The same inadequacy was not noted in vials and ampules. This inadequacy is believed to result because of losses of MTG during compounding, and the greater air to liquid ratio found in Tubex plus the less efficient nitrogen flushing techniques available for Tubex.

TABLE I

| 17 MONTHS STABILITY KLEET VALUES* FILLED TUBEX STORED AT 35° OR 45° | | | | | | |
|---|---|---|---|---|---|---|
| ANTIOXIDANT | Physical Observations | | | | | |
| SYSTEM | R.T. | 35° | 45° | R.T. | 35° | 45° |
| Production | 26–48 | 55 | 63 | D1–D2 | D2 | D3 |
| MTG 2 mg./cc. | 12 | 85 | 76 | NC | D3 | D3 |

TABLE I-continued

17 MONTHS STABILITY
KLEET VALUES* FILLED TUBEX
STORED AT 35° OR 45°

| ANTIOXIDANT SYSTEM | Physical Observations | | | | | |
|---|---|---|---|---|---|---|
| | R.T. | 35° | 45° | R.T. | 35° | 45° |
| MTG 5 mg./cc. | 7 | 12 | 14 | NC | NC | NC |

*No. 42 Klett filter with Tubex adapter. To convert to conventional Klett tubes, multiply the above value by 1.6
NC —No change (refers to solution color)
D —Darkening (solution) D1 through D5 represents a range of darkening in which D1 is very, very slight darkening and discernible only under optimum conditions, and D3 is just discernible under normal conditions.

In Table II, in each case where MTG is used, the only change from the current product formula was to remove the self-degrading antioxidant system and replace it with MTG. No other changes were made. Each of the above six bulks were placed on storage in filled 1.cc. ampules and 10 cc. vials. In the case of the Tubex, various plunger rubber compositions, identified as A–D were evaluated. In the case of the vials, a 13 mm. closure was evaluated. The attached table presents the physical stability of Tubex stored at 35° and RT for 29 months. Though not reported in the table, no significant changes in pH from initial have been seen in the Tubex.

TABLE II

29 MONTH STORAGE

| | STG TEMP. | Phenergan 50 MTG 5 | | Phenergan 25 MTG 5 | | Phenergan 50 Prior Art | | Phenergan 25 Prior Art | |
|---|---|---|---|---|---|---|---|---|---|
| | | Phy. Ob. | Klett | Phy. Ob. | Klett | Phy. Ob. | Klett | Phy. Ob. | Klett |
| Closure A ½ filled 2 cc | RT | D-1,2 | 47 | NC-D-1 | 26 | D-4 | 244 | D-3 | 112 |
| | 35° | D-3,4 | — | D-3,4 | — | D-4 | — | D-3 | — |
| Closure B ½ filled 2 cc | RT | D-1,2 | 48 | NC-D-1 | 26 | D-4 | 250 | D-3 | 155 |
| | 35° | D-3,4 | 264 | D-3 | 161 | D-4 | — | D-4 | — |
| Closure C ½ filled 2 cc | RT | D-1 | 38 | NC | 18 | | | | |
| | 35° | D-3 | 151 | D-3 | 172 | | | | |
| Closure D ½ filled 2 cc | RT | D-1 | 33 | NC | 15 | | | | |
| | 35° | D-3 | — | D-3 | — | | | | |
| Closure A 1 cc filled | RT | D-1 | 36 | NC-D-1 | 27 | D-3 | 190 | D-3 | 106 |
| | 35° | D-3 | — | D-3 | 102 | D-4 | — | D-3 | — |
| Closure B 1 cc filled | RT | D-1 | 37 | NC-D-1 | 27 | D-4 | 240 | D-3 | 115 |
| | 35° | D-4 | — | D-4 | — | D-4 | — | D-3 | — |
| Closure C 1 cc filled | RT | D-1 | 35 | NC | 19 | | | | |
| | 35° | D-4 | — | D-3 | — | | | | |
| Closure D 1 cc filled | RT | D-1 | 33 | NC | 15 | | | | |
| | 35° | D-3 | — | D-4 | — | | | | |
| 1 cc Ampul | RT | NC | — | NC | — | NC | — | NC | — |
| | 35° | NC | — | NC | — | NC | — | NC | — |

Klett values were obtained using No. 42 filter.

Tables I and II conclusively show that levels of 5 mg/cc of MTG impart improved stability to the promethazine hydrochloride formation in reference to oxidative decomposition.

The data presented in the attached table contains data obtained from 35° C. and RT storage after 29 months. The 5° C. data has been left out because in all cases with the MTG formulation, no change from initial was noted. A great difference is noted, especially at room temperature, when comparing the MTG formulation to the prior art. The MTG formulation is much superior. Though not presented in the table, after 5 months at 35° C. and 45° C., in Tubex formulations incorporating 2 mg/ml of MTG, a large amount of shading (varying degrees of darkening) was noted in the Tubex. This might be partially blamed on erratic flushing or more likely a borderline amount of antioxidant. For this reason the level of 5 mg/ml of MTG is considered more desirable for the Tubex product.

The terms and expressions which have been employed are used as terms of description and not of limitation. There is no intention in the use of such terms and expressions, of excluding any equivalents of the feature shown and described or portions thereof, but it is recognized that various modifications are possible within the scope of the invention claimed.

What is claimed is:

1. A therapeutic composition of matter containing up to 50 milligrams per cubic centimeter of an active ingredient selected from the group consisting of promethazine and its pharmaceutically acceptable acid addition salts in a pharmaceutical carrier stabilized with at least 2 milligrams per cubic centimeter of monothioglycerol.

2. A therapeutic composition as defined in claim 1 in which the monothioglycerol is present in the amount of at least 5 milligrams per cubic centimeter.

3. A therapeutic composition of matter containing 25 to 50 milligrams per cubic centimeter of an active ingredient selected from the group consisting of promethazine and its pharmaceutically acceptable acid addition salts in a pharmaceutical carrier stabilized with 2 to 5 milligrams per cubic centimeter of monothioglycerol.

4. An aqueous solution containing up to 50 milligrams per cubic centimeter of promethazine stabilized with at least 2 milligrams per cubic centimeter of monothioglycerol.

5. A stabilized solution as described in claim 4 in which the amount of monothioglycerol is at least 5 milligrams per cubic centimeter.

6. An oxygen-stabilized aqueous solution for use in vials and ampules containing up to 50 milligrams per cubic centimeter of an active ingredient selected from the group consisting of promethazine and its pharmaceutically acceptable acid addition salts in which the stabilizer is at least 2 milligrams per cubic centimeter of monothioglycerol.

7. An oxygen-stabilized aqueous solution for injection containing up to 50 milligrams per cubic centimeter of an active ingredient selected from the group consisting of promethazine and its pharmaceutically acceptable acid addition salts in which the stabilizer is at least 5 milligrams per cubic centimeter of monothioglycerol.

8. An aqueous solution of a promethazine salt stabilized with at least 4 percent by volume of monothioglycerol based on the volume of promethazine.

9. A stabilized aqueous solution as defined in claim 8 in which the monothioglycerol is at least 10 percent by volume per volume.

10. A composition having the recipe:

| | |
|---|---|
| Promethazine hydrochloride | 25–50 mg. |
| EDTA disodium | 0.099 mg. |
| Calcium Chloride | 0.039 mg. |
| Sodium acetate | 6.15 mg. |

-continued

| | |
|---|---|
| Phenol | 5.0 mg. |
| Buffer to adjust to | pH 5.0 |
| Monothioglycerol | 5–6 mg. |
| Water to make | 1.0 cc. |

* * * * *